United States Patent
Nam et al.

(10) Patent No.: US 9,494,453 B2
(45) Date of Patent: Nov. 15, 2016

(54) ULTRASONIC SENSOR FOR HIGH TEMPERATURE AND MANUFACTURING METHOD THEREOF

(71) Applicants: WOOJIN INC., Hwaseong-si (KR); SONIC CORPORATION, Tokyo (JP)

(72) Inventors: Ki Han Nam, Hwaseong-si (KR); Hyeon Kyu Joo, Hwaseong-si (KR); Minehiro Tonosaki, Tokyo (JP); Fumiyasu Ikarashi, Tokyo (JP); Hideo Kawaguchi, Tokyo (JP); Noriaki Saito, Tokyo (JP)

(73) Assignees: WOOJIN INC., Hwaseong-Si (KR); SONIC CORPORATION, Tokyo (JP)

( * ) Notice: Subject to any disclaimer, the term of this patent is extended or adjusted under 35 U.S.C. 154(b) by 0 days.

(21) Appl. No.: 14/398,374

(22) PCT Filed: Mar. 25, 2014

(86) PCT No.: PCT/KR2014/002488
§ 371 (c)(1),
(2) Date: Oct. 31, 2014

(87) PCT Pub. No.: WO2014/157907
PCT Pub. Date: Oct. 2, 2014

(65) Prior Publication Data
US 2016/0003654 A1    Jan. 7, 2016

(30) Foreign Application Priority Data
Mar. 25, 2013  (KR) .................. 10-2013-0031672

(51) Int. Cl.
*G01F 1/66* (2006.01)
*G01N 29/22* (2006.01)
(Continued)

(52) U.S. Cl.
CPC ............. *G01F 1/662* (2013.01); *G01F 1/66* (2013.01); *G01N 29/22* (2013.01); *G01N 29/228* (2013.01); *G01N 29/245* (2013.01); *H04R 17/00* (2013.01)

(58) Field of Classification Search
CPC ......... G01F 1/66; G01F 1/662; G01N 29/22; G01N 29/228; G01N 29/245; H04R 17/00; H04R 17/10; G01L 23/10; H03H 9/02559; H03H 9/02015; B06B 1/067
See application file for complete search history.

(56) References Cited

U.S. PATENT DOCUMENTS 3,591,813 A * 7/1971 Coquin ................... H01L 41/18
                                                        252/62.9 R
4,297,607 A * 10/1981 Lynnworth ............. B06B 1/067
                                                        310/327
(Continued)

FOREIGN PATENT DOCUMENTS

JP          62006598 A   *  1/1987
JP          04-029056        1/1992
(Continued)

OTHER PUBLICATIONS

English Translation of International Search Report from PCT/KR2014/002488; dated May 26, 2014.
(Continued)

*Primary Examiner* — Daniel J Colilla
(74) *Attorney, Agent, or Firm* — Baker & Hostetler LLP (57) ABSTRACT

Provided is an ultrasonic sensor which includes a piezoelectric vibrator made of a lithium niobate (LN) single crystal and may be used in a high temperature region by generating a high ultrasonic wave output, and prevents cracks from being generated in the crystal. A piezoelectric vibrator 1 of the present invention has a surface (Y-axis 36° cut surface) obtained by rotating a surface orthogonal to a Y-axis of the LN crystal about an X-axis by 36°±2° as an output surface. The ultrasonic sensor further includes a retarder 3 made of titanium and a bonding layer 2 for bonding one surface of the retarder 3 to the output surface. The bonding layer 2 is made of silver and frit glass, and the frit glass has a coefficient of linear expansion ranging from $5\times10^{-6}$ $K^{-1}$ to $15\times10^{-6}$ $K^{-1}$.

9 Claims, 4 Drawing Sheets (51) Int. Cl.
*H04R 17/00* (2006.01)
*G01N 29/24* (2006.01)

(56) References Cited

U.S. PATENT DOCUMENTS

| | | | |
|---|---|---|---|
| 4,961,347 A | 10/1990 | Arakawa et al. | |
| 2005/0016298 A1* | 1/2005 | Hill | B06B 1/067 |
| | | | 73/863.03 |
| 2007/0205697 A1 | 9/2007 | Chaggares et al. | |
| 2011/0291525 A1* | 12/2011 | Maruyama | H02N 2/0015 |
| | | | 310/334 |

FOREIGN PATENT DOCUMENTS

| JP | 07-046095 | 2/1995 |
|---|---|---|
| JP | 10-339722 | 12/1998 |
| JP | 11-054531 A | 2/1999 |
| JP | 2000-162004 | 6/2000 |
| JP | 2005-064919 | 3/2005 |
| JP | 2006-090804 | 4/2006 |
| JP | 2008-1602092 A | 7/2008 |
| JP | 2008-256423 | 10/2008 |
| KR | 10-2004-0089484 A | 10/2004 |
| KR | 10-2011-0079096 A | 7/2011 |

OTHER PUBLICATIONS

R. Kazys, et al., "Research and development of radiation resistant ultrasonic sensors for quasi-image forming systems in a liquid lead-bismuth," ISSN 1392-2114 Ultragarsas (Ultrasound), vol. 62, No. 3, pp. 7-15, 2007.

Q. F. Zhou, et al., "Design and modeling of inversion layer ultrasonic transducers using LiNbO3 single crystal," Ultrasonics, vol. 44, Supplement, pp. e607-e611, 2006.

Ikeda Dakuro, "Basis of Piezoelectric Material", OHM Co. 1984.

K. K. Wong edit, "Properties of Lithium Niobate," EMIS datareviews series No. 28, Inspec, 2002.

* cited by examiner

ULTRASONIC SENSOR FOR HIGH TEMPERATURE AND MANUFACTURING METHOD THEREOF

CROSS-REFERENCE TO RELATED APPLICATIONS

This application is a National Stage of International Patent Application No. PCT/KR2014/002488, filed Mar. 25, 2014 and claims priority to foreign application KR 10-2013-0031672, filed Mar. 25, 2013, the contents of which are incorporated herein by reference in their entirety.

TECHNICAL FIELD

The present invention relates to an ultrasonic sensor, and more particularly, to an ultrasonic sensor suitable for measuring a flow rate of a high-temperature fluid and a manufacturing method thereof.

BACKGROUND ART

An ultrasonic flowmeter emits an ultrasonic wave into a fluid, receives the emitted ultrasonic wave to obtain a flow velocity, and converts the obtained flow velocity into a flow rate of a fluid to measure the flow rate (Non-Patent Document 1). An ultrasonic sensor which is a piezoelectric vibrator is used to emit or receive the ultrasonic wave. As a method of obtaining the flow velocity, there is a method using a Doppler effect, and the like. However, a method for measuring a transfer time difference, which uses ultrasonic sensors disposed at an upstream side and a downstream side of a pipe, respectively, and includes: obtaining a flow velocity based on a difference between a propagation time of an ultrasonic wave transmitted to the upstream side and a propagation time of an ultrasonic wave transmitted to the downstream side; and calculating the flow rate by the obtained flow velocity, has been widely used.

The method for measuring the transfer time difference uses a gate configured to measure time based on an ultrasonic wave transmitting timing and an ultrasonic wave receiving timing between the ultrasonic sensors disposed at the upstream and downstream sides of the pipe, and a high speed counter to measure an ultrasonic propagation time to the upstream side and an ultrasonic propagation time to the downstream side. As a timing detecting method, there is a zero-crossing method to measure a position at which the received ultrasonic signal is zero-crossed.

Meanwhile, a correlation method obtains the propagation time to the upstream side and the propagation time to the downstream side based on an autocorrelation peak time of a transmission waveform and a reception waveform.

The ultrasonic flowmeter has also been used in equipments such as a boiler to measure a flow rate of a fluid under high temperature and high pressure conditions. When an outlet temperature of the boiler is about 100° C., a sensor using piezoelectric zirconate titanate (PZT) which is piezoelectric ceramic has been mainly used in the related art. However, a Curie point of the PZT is about 150 to 250° C. depending on a composition thereof, and a piezoelectric constant thereof is remarkably reduced in the vicinity of the Curie point. For this reason, in order to measure a flow rate of a fluid in a region exceeding 200° C., a sensor using a piezoelectric material or a piezoelectric single crystal material having a higher Curie point than the PZT has been used (Non-Patent Document 2).

As the method of ultrasonic flow measurement in a high temperature region, a method using a sensor of a conventional PZT based material by cooling the sensor has been proposed. For example, Patent Document 1 discloses a method for obtaining a flow rate of a high temperature fluid according to a transfer time difference principle by disposing a pipe through which the high temperature fluid flows within a container filled with a low temperature liquid and disposing ultrasonic sensors on pipe walls of the upstream and downstream sides of the pipe so that the ultrasonic sensors are cooled by the low temperature liquid. Further, Patent Document 2 discloses a configuration to prevent a temperature of the piezoelectric vibrator from increasing due to heat from the high temperature fluid by installing a sound transmission passage of a quartz material between the piezoelectric vibrator and the high temperature fluid at the time of measuring the flow rate of the high temperature fluid.

Figure 1:
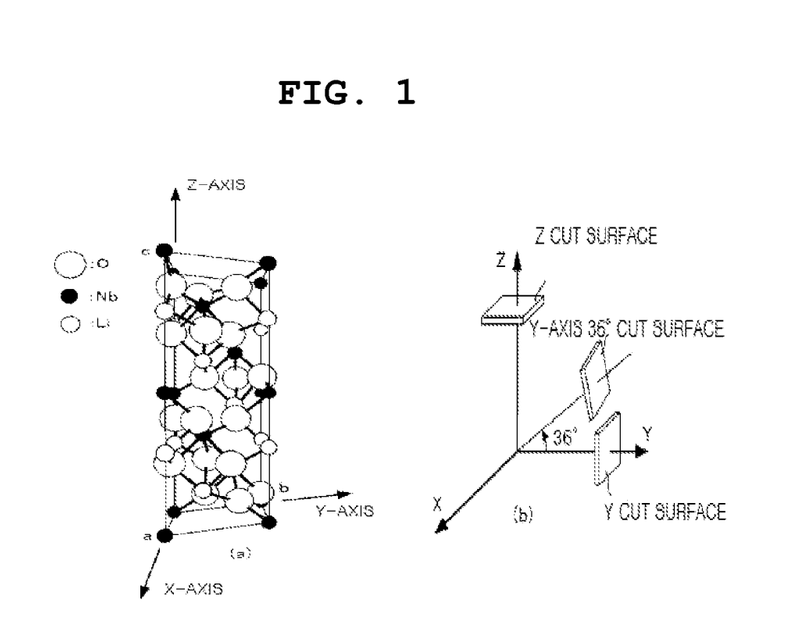

Meanwhile, as a piezoelectric material, there is lithium niobate (LiNbO$_3$: hereinafter briefly referred to as an LN) which has a much higher Curie point than the PZT and may withstand high temperature conditions. General properties of the LN are described in Non-Patent Document 5. The Curie point of the LN is about 1200° C. FIG. 1(a) illustrates a crystal structure of the LN. The LN has a crystal structure of a trigonal system and as illustrated in FIG. 1, an X-axis, a Y-axis, and a Z-axis are crystallographically defined. Further, as a lattice constant of the LN, a=b=5.148 Å and c=13.863 Å.

When the LN is used as the ultrasonic sensor of the ultrasonic flowmeter, an ultrasonic wave having a short duration needs to be generated as a burst wave and thus vibration needs to be dumped. In order to dump the vibration, a metal piece (that is, dumper) is attached to the LN vibrator. As the attachment position of the metal piece, there are two cases, that is, a case in which the metal piece is attached on the same surface as an output surface of the ultrasonic wave in the ultrasonic sensor as described in Patent Document 4, or the like, and a case in which the metal piece is attached on a surface opposite to the output surface of the ultrasonic wave as described in Patent Document 5, or the like. Patent Document 4 discloses that an aluminum alloy lead material is used for bonding the dumping portion to the piezoelectric vibrator, and Patent Document 5 discloses that silver (Ag) is used as the dumping portion for bonding the dumping portion to the piezoelectric vibrator by eutectic bonding between thin films of silver and gold (Au). Further, Patent Document 7 discloses that a metal shoe which forms a temperature gradient while serving as the dumping portion is bonded to the piezoelectric vibrator made of a ferroelectric material having a high Curie point. In addition, Patent Document 10 discloses that as a lead material for performing the bonding to the LN piezoelectric vibrator, an Al—Si—Mg alloy or a silver solder is used and as the silver solder, a material containing 45% Ag, 16% Cu, 24% Cd and the remainder being Zn is used. Further, Patent Document 10 discloses that when the LN piezoelectric vibrator is bonded to a protective layer made of a cermet insulating material, a thin film of Cu or Ni is formed on a surface of the cermet insulating material by an ion plating, a silver electrode is formed on the piezoelectric vibrator, and then the silver electrode of the piezoelectric vibrator is bonded to the cermet insulating material by the silver solder.

When a single crystal of the LN which is the trigonal system is thermally expanded, anisotropy is present in a coefficient of linear expansion, and even though the coefficient of linear expansion in an X-axis direction and the coefficient of linear expansion in a Y-axis direction are the same, the coefficient of linear expansion in a Z-axis direction is different therefrom. Considering that the metallic dumping portion is bonded to the piezoelectric vibrator made of the LN single crystal, when the dumping portion is bonded to a surface other than a surface (so called "Z cut surface") orthogonal to the Z-axis in the LN, the anisotropy occurs within the bonded surface during the thermal expansion, and therefore cracks may be generated in the piezoelectric vibrator due to a heat cycle applied thereto, and the like. However, as described in Non-Patent Document 3 and the like, a piezoelectric coefficient in the Z-axis direction in the LN single crystal is smaller than that of other general piezoelectric materials. For this reason, the ultrasonic sensor, in which the LN piezoelectric vibrator is not damaged even if the heat cycle is applied thereto, has reduced transmission or reception capabilities of the ultrasonic wave and does not accurately measure the flow rate. Table 1 shows characteristics such as the Curie point, the piezoelectric coefficient, and a relative dielectric constant, in various piezoelectric materials, and Table 2 shows a coefficient thermal expansion (coefficient of linear expansion) in the LN or other materials. In the Table 1, a Z cut plate represents an LN plate cut along two parallel Z cut surfaces and a Y 36° cut plate represents the LN plate cut along two paralell Y-axis 36° cut surfaces to be described below.

TABLE 1

| Piezoelectric Material | LiNbO$_3$ (Y 36° cut plate) | LiNbO$_3$ (Z cut plate) | PbNb$_2$O$_6$ | PbTiO$_3$ | PZT |
|---|---|---|---|---|---|
| Curie Point (° C.) | 1150 | 1150 | 530 | 385 | 150 to 295 |
| Piezoelectric Coefficient D$_{33}$ (pC/N) | 40 | 6 | 80 | 44 | 470 |
| Relative Dielectric Constant ε | 39 | 29 | 300 | 185 | 1500 to 3000 |
| Density (g/cm$^3$) | 4.46 | 4.46 | 5.7 | 7.6 | 7.65 |
| Sound Velocity (m/s) | 7340 | 3800 | — | 4500 | 4600 |

TABLE 2

| Material | Coefficient of Linear Expansion at 25 to 850° C. ($\times 10^{-6}$ K$^{-1}$) |
|---|---|
| LiNbO$_3$ (X-axis direction, Y-axis direction) | 5.15 to 2.25 |
| LiNbO$_3$ (Z-axis direction) | 13.85 to 3.88 |
| Silver | 18.9 or more |
| Stainless Steel (SUS304) | 14.8 |
| Pure Titanium | 8.4 or more |
| Frit glass (SiO$_2$—B$_2$O$_3$—ZnO) | 7.65 |

When the flowmeter is configured using the ultrasonic wave, for example, it is necessary for the ultrasonic sensor to be mechanically and acoustically bonded to the pipe or a spool piece installed on the pipe. In this case, the ultrasonic wave from the ultrasonic sensor needs to be efficiently transferred to the pipe, the spool piece, or the like, and therefore a couplant (contact medium) is applied to a contact portion of the pipe, the spool piece, or the like. When the flowmeter for high temperature is manufactured, as the couplant, a material withstanding high temperature is used. For example, Patent Documents 6 to 8 disclose a couplant which includes water glass as a main ingredient and has appropriate flexibility or viscosity in a measurement temperature region. After the ultrasonic sensor is manufactured, the couplant including the water glass as a main ingredient is disposed to the ultrasonic sensor by application, or the like. Patent Document 9 also discloses that an electrode made of a heat resistant soft metal having appropriate plasticity in the measurement temperature region and the electrode is used as the couplant. Further, as the couplant for high temperature, examples using a gold foil or a copper foil and silver have been known in the related art.

The ultrasonic flowmeter is used a principle of obtaining a flow velocity based on, for example, the difference between the ultrasonic transfer time in a flow direction and the ultrasonic transfer time in a direction opposite to the flow direction, and measuring the flow rate by the obtained flow velocity (Non-Patent Document 1). Therefore, it is preferable that the ultrasonic flowmeter has a small Q value for the ultrasonic signal and small reverberation as a whole of the ultrasonic flowmeter. When the zero-crossing method or the correlation measurement method is used for measuring the transfer time difference, it is important to reduce, in particular, the reverberation.

To reduce the reverberation, for example, a thin protective film or a retarder is disposed on a front surface of an ultrasonic probe for nondestructive inspection or medical treatment. The retarder also serves as the above-described dumping portion. When an acoustic impedance (herein, referred to as an "intrinsic acoustic impedance" represented by a product of the sound velocity and the density of the material) of the retarder is close to the acoustic impedance of the piezoelectric vibrator, the ultrasonic wave generated from the piezoelectric vibrator is transferred to the retarder and vibration energy disappears by being scattered in the vibrator. Therefore, multiple reflections, that is, resonances are rapidly damped within the vibrator as much. As the acoustic impedance of the vibrator is close to that of the retarder, the vibration energy inside the piezoelectric vibrator is transferred to an outside thereof, and therefore the Q value of the vibrator is reduced and an output waveform thereof becomes a waveform having a small ringing. However, a piezoelectric vibrator having a high Q value has been used in the related art. Patent Document 3 discloses that the reverberation appears to be small by using a propagation auxiliary member in a two vibrator type ultrasonic probe used for nondestructive inspection, or the like.

PRIOR ART DOCUMENT

Patent Document (Patent Document 1) Japanese Patent Laid-Open Publication No. 2000-162004

(Patent Document 2) Japanese Patent No. 4205711

(Patent Document 3) Japanese Patent Laid-Open Publication No. 2006-090804

(Patent Document 4) Japanese Patent Laid-Open Publication No. 7-046095

(Patent Document 5) Japanese Patent Laid-Open Publication No. 10-339722

(Patent Document 6) Japanese Patent Laid-Open Publication No. 4-029056

(Patent Document 7) Japanese Patent No. 4244172

(Patent Document 8) Japanese Patent Laid-Open Publication No. 2005-064919

(Patent Document 9) Japanese Patent Laid-Open Publication No. 2008-256423

(Patent Document 10) Specification of U.S. Pat. No. 4,961,347

Non-Patent Document (Non-Patent Document 1) "(revised version) Practical Navigation of Flowmeter", association of weighing equipment industry society in Japan which is general incorporated association, Kogyogijutsusha Publication, pp 119-126 (September 2012)

(Non-Patent Document 2) R. Kazys, et al., "Research and development of radiation resistant ultrasonic sensors for quasi-image forming systems in a liquid lead-bismuth," ISSN 1392-2114 ULTRAGARSAS (ULTRASOUND), Vol. 62, No. 3, pp. 7-15, 2007

(Non-Patent Document 3) Q. F. Zhou, et al., "Design and modeling of inversion layer ultrasonic transducers using $LiNbO_3$ single crystal," Ultrasonics, Vol. 44, Supplement, pp. e607-e611, 2006

(Non-Patent Document 4) Ikeda Dakuro, "Basis of Piezoelectric Material", OHM Co. 1984

(Non-Patent Document 5) K. K. Wong edit, "Properties of Lithium Niobate," EMIS datareviews series No. 28, INSPEC, 2002

DISCLOSURE

Technical Problem

When configuring an ultrasonic sensor available in a high temperature region using the piezoelectric vibrator made of lithium niobate (LN), in order to prevent the vibrator from being damaged in consideration of the coefficient of thermal expansion and the anisotropy of the LN, a piezoelectric vibrator, which has a surface (Z cut surface) orthogonal to the Z-axis of the crystal as an output surface of the ultrasonic wave, has been used the related art. However, since the piezoelectric constant in the Z-axis direction in the LN is small, the ultrasonic wave may not be generated at a high output, and thereby it is not possible to detect the ultrasonic wave with high sensitivity.

As an orientation having a large piezoelectric constant in the LN, an orientation in which the Y-axis of the crystal rotates to the vicinity of the X-axis by about +36° (for example, 36°±2°) has been known in the related art (for example, Non-Patent Document 3). In order to obtain an ultrasonic sensor having a high ultrasonic wave output and high sensitivity of ultrasonic wave, an ultrasonic sensor, which is configured in such a manner that a surface (hereinafter referred to as a "Y-axis 36° cut surface") orthogonal to a direction in which the Y-axis rotates to the vicinity of the X-axis by about +36° is formed as the output surface of the ultrasonic wave, may be considered. FIG. 1(b) describes the Y-axis 36° cut surface of the LN and illustrates that the Y-axis 36° cut surface may be obtained by rotating the surface (Y cut surface) orthogonal to the Y-axis to the vicinity of the X-axis by +36°. FIG. 1(b) also illustrates the Z cut surface for reference. However, since the coefficient of linear expansion is different in two in-plane directions in a surface other than the Z cut surface, that is, a surface which is set an inclined direction in the Z-axis direction as a normal surface, a uniform coefficient of linear expansion may be obtained and when for example, the retarder or the dumping member is bonded to the surface, cracks may be generated in the crystal. Therefore, there is a need to form the Y-axis 36° cut surface as the output surface and develop a bonding method for preventing cracks from being generated in the crystal when the retarder, and the like is boned thereto. A detailed value for the coefficient of linear expansion at the Y-axis 36° cut surface may not be found, but is considered to be an intermediate value between the coefficient of linear expansion in the Z-axis direction and the coefficient of linear expansion in the X-axis direction (the coefficients of linear expansion in the X-axis direction and the Y-axis direction are the same). In consideration of an inclined angle from the Z-axis, the value may be estimated as about 7 to $10 \times 10^{-6}$ $K^{-1}$.

When the Y-axis 36° cut surface is formed as the output surface, the crystal is bonded to the retarder by a bonding material to prevent cracks from being generated in the crystal, and therefore in a range of temperature applied during the bonding or a use temperature range of the ultrasonic sensor, it is necessary for the crystal, the retarder, and the bonding material to have a value of the coefficients of linear expansion approximate each other.

Further, in the above-described conventional ultrasonic sensor, a couplant (contact medium) needs to be disposed between the pipe or the spool piece to which the sensor is attached and the output surface of the ultrasonic wave (for example, an emission end face of the ultrasonic wave) to improve mechanical coupling in terms of the ultrasonic wave. In a conventional ultrasonic sensor for high temperature, it is difficult to rapidly dispose the ultrasonic sensor in the pipe or the spool piece which is an object to be inspected by additionally applying or attaching couplant materials such as a gold foil, a copper foil, an aluminum foil, a polyimide foil, and water glass to the ultrasonic sensor later. Therefore, a method for forming a soft metal serving as the couplant on the output surface of the ultrasonic wave during manufacturing the ultrasonic sensor is required.

It is necessary for the ultrasonic sensor to improve measurement precision by using a single crystal which may suitably separate a longitudinal wave and a transverse wave from each other to propagate a high-quality signal. It has been known that it is effective to bond the titanium retarder to the piezoelectric vibrator, but if the bar-shaped titanium retarder is bonded to a single crystal LN, the ultrasonic wave from an end face at a side opposite to the bonded surface in the retarder is multi-reflected, and thus a phase thereof is inverted 180°. For this reason, the reflection wave thereof as reverberation overlaps an original ultrasonic transfer signal to cause deterioration in signal processing for measurement. In particular, when using the zero-crossing method or the correlation method to measure the transfer time difference, if the multiple reflection waves overlap the original received signal under any circumstances, it is not possible to accurate measure the flow rate.

Accordingly, in consideration of the above-described circumstances, it is an object of the present invention to provide an ultrasonic sensor which includes a piezoelectric vibration generating a high ultrasonic wave output by having a Y-axis 36° cut surface of LN as an output surface and may be used in a high temperature region and prevent cracks from being generated in a crystal, and a manufacturing method thereof.

Technical Solution

According to one aspect of the present invention, there is provided an ultrasonic sensor, including: a piezoelectric vibrator which is made of lithium niobate and has a Y-axis 36° cut surface as an output surface; a retarder made of titanium; and a bonding layer for bonding one surface of the retarder to the output surface, wherein the bonding layer is made of silver and frit glass, and the frit glass has a coefficient of linear expansion ranging from $5\times10^{-6}$ $K^{-1}$ to $15\times10^{-6}$ $K^{-1}$.

According to another aspect of the present invention, there is provided a manufacturing method of an ultrasonic sensor having lithium niobate as a piezoelectric vibrator, including: forming the piezoelectric vibrator which has a Y-axis 36° cut surface as an output surface, and is prepared by applying a silver paste to at least the output surface and burning the same; applying the silver paste to one surface and the other surface of a titanium retarder which are opposite to each other; and contacting one surface of the retarder with the output surface of the burned piezoelectric vibrator, and then performing burning the same under an inert gas atmosphere at a predetermined temperature or more, wherein the silver paste applied to the output surface and the one surface of the retarder includes silver and frit glass, and the frit glass has a coefficient of linear expansion ranging from $5\times10^{-6}$ $K^{-1}$ to $15\times10^{-6}$ $K^{-1}$.

In the present invention, the Y-axis 36° cut surface is referred to a surface obtained by rotating a surface orthogonal to the Y-axis of the LN crystal about the X-axis by about +36° (for example, 36°±2°).

Further, an example of the inert gas may include nitrogen and argon and the predetermined temperature may be, for example, 500° C.

Advantageous Effects

According to the present invention, by using the silver and frit glass materials for bonding the LN piezoelectric vibrator to the titanium retarder, the Y-axis 36° cut surface capable of providing high output may be used as the output surface of the LN piezoelectric vibrator without damaging the piezoelectric vibration, and the like even when used in the high temperature conditions.

DESCRIPTION OF DRAWINGS

FIG. 1(a) is a diagram illustrating a crystal structure of lithium niobate (LN) and (b) is a diagram for describing a Y-axis 36° cut surface of LN.

FIGS. 2(a) and (b) are a top view and a side view of an ultrasonic sensor which is one embodiment of the present invention, respectively.

FIGS. 7(a) and (b) are graphs for describing an angle of beam spread.

FIGS. 8(a) and (b) are graphs for describing a multiple reflection waveform.

BEST MODE

Figure 2:
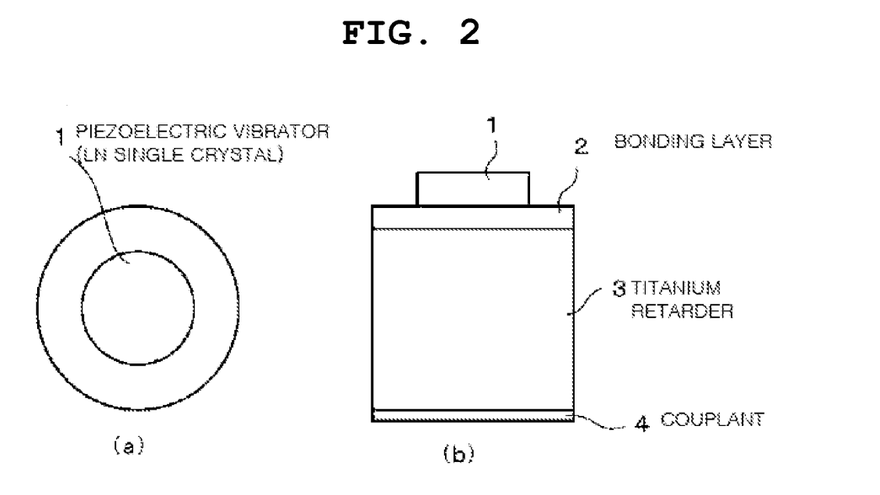

Hereinafter, embodiments of the present invention will be described with reference to the accompanying drawings. FIG. 2 illustrates an ultrasonic sensor which is one embodiment of the present invention.

The ultrasonic sensor includes a single crystal of lithium niobate (LN: $LiNbO_3$) as a piezoelectric vibrator 1. The piezoelectric vibrator 1 has a disk shape. In the piezoelectric vibrator 1, both of a bottom surface and a top surface which are formed in a disk are a Y-axis 36° cut surface of LN. In addition, one surface (bottom surface in FIG. 2) of two surfaces (the above-described bottom and top surfaces) of the piezoelectric vibrator 1 which face each other is an output surface through which an ultrasonic wave is output from the piezoelectric vibrator 1. The output surface is bonded to one end of a round bar-shaped titanium retarder 3 through a bonding layer 2. The titanium retarder 3 is formed of pure titanium (Ti). First of all, the titanium retarder 3 may inevitably include impurities contained in titanium. The bonding layer 2 is formed by burning a silver paste including frit glass as described below. Therefore, the bonding layer 2 is made of silver and frit glass. Herein, the frit glass having a coefficient of linear expansion ranging from $5\times10^{-6}$ $K^{-1}$ to $15\times10^{-6}$ $K^{-1}$ is used. The other end of the titanium retarder 3 is provided with a couplant 4 including silver. In order to form the couplant of the ultrasonic sensor simultaneously with manufacturing a main body of the sensor without subsequently adding the couplant, it is preferable that the couplant 4 having the same composition as that of the bonding layer 3 is simultaneously formed with the bonding layer 3.

Figure 3:
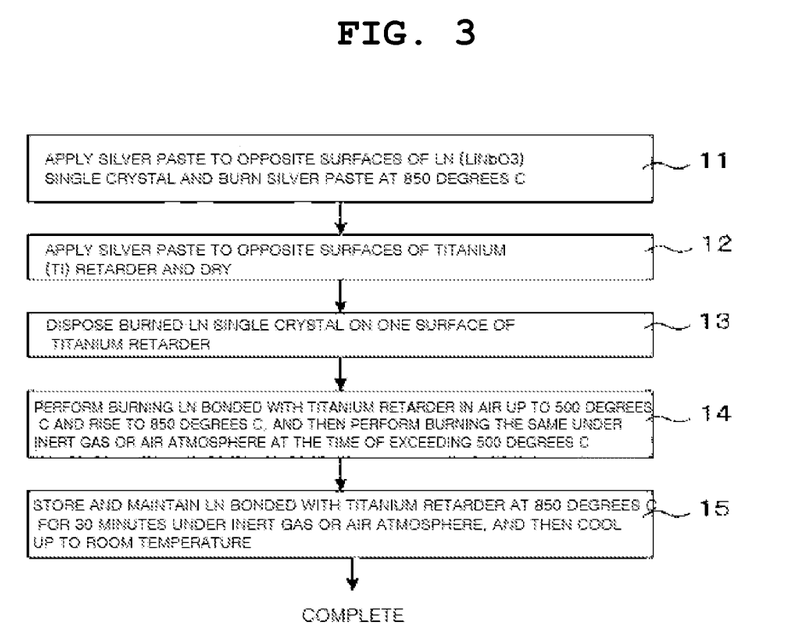
FIG. 3 is a flow chart illustrating a manufacturing process of the ultrasonic sensor illustrated in FIG. 2.

FIG. 3 illustrates an example of a manufacturing process of the ultrasonic sensor.

For example, opposite surfaces of the LN single crystal (piezoelectric vibrator 1) having a thickness of 0.8 mm to 1.6 mm and a diameter of 10 mm to 18 mm are applied with the silver paste for an electrode and are burned at 700 to 850° C. (step 11). Further, both end faces of a round bar (diameter of 20 mm and length of 20 mm) of the titanium retarder 3 made of a pure titanium material are applied with the silver paste and dried at 80° C. (step 12). Further, contacts a tip portion of the titanium retarder 3 with the LN single crystal (piezoelectric vibrator 1) having the burned electrode (step 13), and performs burning the same as a whole (step 14). For the burning, an inert atmospheric burning furnace is used and the LN bonded with the titanium retarder is stored and maintained in the air for a period until a temperature in the burning furnace reaches 500° C., that is, for 3 hours to evaporate a binder ingredient included in the silver paste. Next, the temperature in the burning furnace rises from 500° C. to a range of 700 to 850° C. for 2 hours under the inert gas or the air atmosphere. The reason of maintaining the burning furnace in the inert gas or the air atmosphere is to prevent a titanium oxide layer from being formed in the bonding layer 2 or control the oxide layer. As the inert gas, for example, argon (Ar), nitrogen ($N_2$), a mixed gas thereof may be used. The LN bonded with the titanium retarder is stored and maintained at 700 to 850° C. for 30 minutes and then is cooled to a room temperature for 10 hours under the inert gas or the air atmosphere (step 15). The ultrasonic sensor according to the present embodiment is completed by the above-described process.

According to the present invention, the titanium retarder 3 is bonded to the Y-axis 36° cut surface of LN. Herein, in order to prevent a damage in the piezoelectric vibrator (LN crystal) 1, the bonding using a silver paste containing frit glass is performed. In this case, the silver paste used herein includes 79 to 82% of silver and 2.3 to 2.5% of frit glass ingredient, in terms of a mass ratio, and an organic binder ingredient as a balance. The organic binder ingredient mainly includes diethyleneglycol mono n-butyl ether or ethyl cellulose.

According to the present embodiment, kinds of frit glass mixed with the silver paste may include, for example, $SiO_2$—$ZnO$—$B_2O_3$ (zinc borosilicates) and $B_2O_3$—$ZnO$—$Al_2O_3$ (zinc alumina borates), and materials having a coefficient of linear expansion ranging from $5 \times 10^{-6}$ $K^{-1}$ to $15 \times 10^{-6}$ $K^{-1}$, preferably 7 to $8 \times 10^{-6}$ $K^{-1}$ may be used. In this case, a composition of the silver paste may include 82% of Ag, 0.1% of Si, 0.05% of Al, 0.2% of B, and 1.0% of Zn, in terms of mass %. Further, the frit glass may be ($Al_2O_3$—$B_2O_3$—$ZnO$—$CoO$—$K_2O$—$CaO$—$SnO$)—$SiO_2$ based frit glass and materials having a coefficient of linear expansion of $7.6 \times 10^{-6}$ $K^{-1}$ may be used. In this case, a composition of the silver paste may include 81% of Ag, 0.4% of Si, 0.2% of Al, 0.2% of B, 0.01% of Zn, and 0.02% of Co, in terms of mass %. According to the reviews of the present inventors, the frit glass including cobalt is preferably used. As can be seen from the above Table 2, the coefficient of linear expansion of the glass ingredient is $7.65 \times 10^{-6}$ $K^{-1}$, which is close to a coefficient of linear expansion of titanium material of $8.4 \times 10^{-6}$ $K^{-1}$. For the coefficient of linear expansion after the silver paste is burned, the coefficient of linear expansion of glass having $7.65 \times 10^{-6}$ $K^{-1}$ is dominant compared to the coefficient of linear expansion of silver having $18.9 \times 10^{-6}$ $K^{-1}$. For this reason, the ultrasonic sensor according to the present embodiment has in-plane anisotropy in the coefficient of linear expansion at the Y-axis 36° cut surface of LN to prevent the bonded portion from delaminating or cracks from being generated in the crystal. According to the present embodiment, the bonding layer 2 has a thickness of, for example, 10 μm to 30 μm and the couplant 4 has a layer thickness of 5 μm to 20 μm.

Hereinafter, the material of the retarder will be described. The ultrasonic sensor according to the present embodiment is manufactured by the above-described process. Herein, in order to reduce thermal oxidation in a temperature range of 500 to 850° C. subjected during bonding the retarder to the piezoelectric vibrator and in the viewpoint of processing property, pure titanium, not stainless steel, is used. For the coefficient of linear expansion, the pure titanium has a coefficient of linear expansion having $8.4 \times 10^{-6}$ $K^{-1}$ closed to a coefficient of linear expansion having 7 to $10 \times 10^{-6}$ $K^{-1}$ which is considered at the Y-axis 36° cut surface of LN. According to the reviews of the present inventors, when the retarder is made of a titanium alloy, a difference between the coefficients of linear expansion of the piezoelectric vibrator and the retarder is increased and therefore it is believed that the delaminating of the bonded portion, the damage in the crystal, or the like may easily occur.

Figure 4:
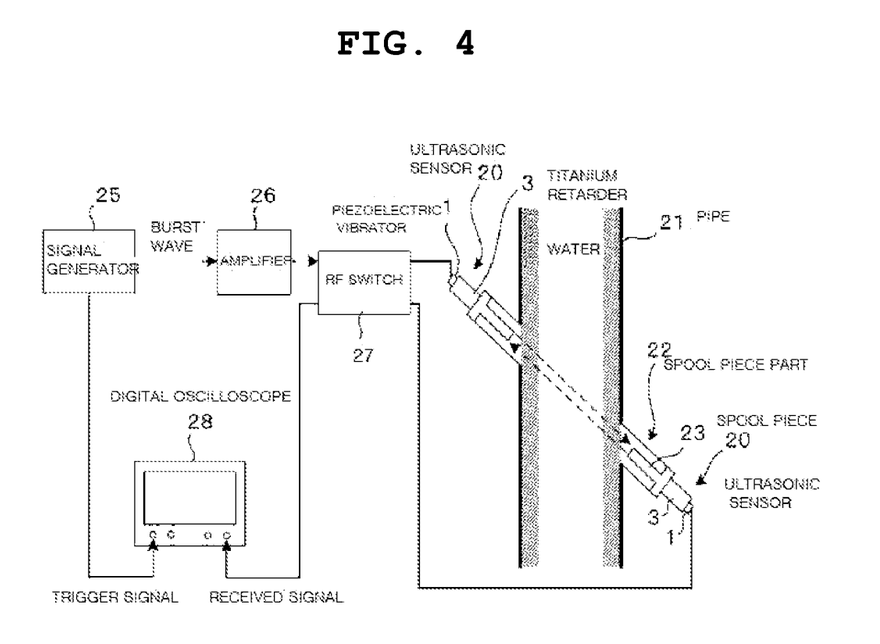
FIG. 4 is a diagram illustrating a transmitting and receiving configuration for measuring a flow rate.

FIG. 4 illustrates a configuration for measuring a flow rate using the ultrasonic sensor according to the present embodiment. Herein, hot water flowing in a pipe 21 is an object to be measured the flow rate. An upstream side and a downstream side of the pipe 21 are mounted with spool piece parts 22, respectively. Each spool piece part 22 has a spool piece 23 which is made of cast iron and configured to transfer an ultrasonic wave to water in the pipe 21. The ultrasonic sensor 20 according to the present embodiment is bonded to the spool piece 23 from the outside so that the spool piece 23 is pressure-welded to the titanium retarder 3 through the couplant 4. Herein, a temperature of the water in the pipe 21 is set to be, for example, 230° C. which is much higher than the boiling point (100° C.) of water under the atmospheric pressure. Since this temperature is closed to a critical point of water, a pressure of the water in the pipe 21 is, for example, 20 MPa.

In the configuration illustrated in FIG. 4, the spool pieces 23 made of cast iron are mounted inside each spool piece part 22 and the ultrasonic sensor 20 is mounted in the spool piece part 22 from the outside, and therefore the ultrasonic sensor 20 does not contact water. However, since the ultrasonic sensor 20 is subjected to heat from the spool piece part 22, it needs to be operated at a high temperature.

Figure 5:
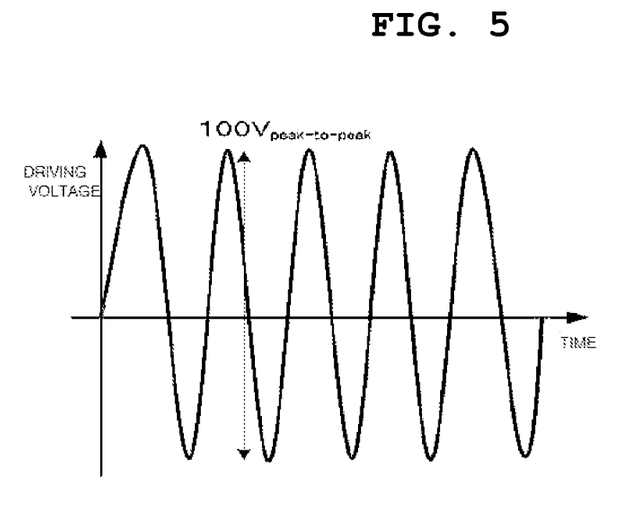
FIG. 5 is a waveform diagram illustrating a burst waveform for driving the ultrasonic sensor.

Herein, the ultrasonic sensor 20 is driven by a burst wave of 4 MHz which is formed of 5 voltage peaks (that is, 5 waves) as illustrated in FIG. 5, and includes a signal generator 25 for generating the burst wave. The burst wave generated from the signal generator 25 is amplified to a sine wave of $100V_{p-p}$ by an amplifier 26 and is transferred to a (high frequency) RF switch 27. The RF switch 27 functions to change transmission and reception between the ultrasonic sensor 20 of the upstream side and the ultrasonic sensor 20 of the downstream side at every 1 ms. When the sensor of the upstream side transmits an ultrasonic burst signal and the sensor of the downstream side receives the burst signal for 1 ms (T1), the sensor of the upstream side receives the ultrasonic burst signal and the sensor of the downstream side transmits the ultrasonic burst signal for subsequent 1 ms (T2). The RF switch 27 outputs the signal received by the ultrasonic sensor at a receiving side, in which the signal is recorded by a 50-ohm terminated digital oscilloscope 28. The digital oscilloscope 28 receives a trigger signal from the signal generator 25. The transfer time difference may be obtained from data recorded in the digital oscilloscope 28, and therefore a flow velocity and a flow rate may be calculated based on a shape of the pipe 21, a disposition of each ultrasonic sensor 20, acoustic nature of the object to be measured (herein, water) from the transfer time difference.

Figure 6:
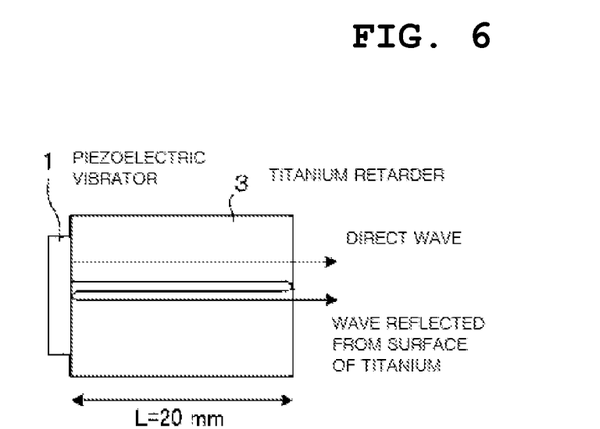
FIG. 6 is a schematic cross-sectional view for describing multiple reflections in the ultrasonic sensor.

Next, the multiple reflections from the end face of the retarder will be described. FIG. 6 describes a principle of the generation of the multiple reflections.

In the end face (end face of the couplant) of a side opposite to a bonded surface between the titanium retarder 3 and the piezoelectric vibrator 1, acoustic impedance is different between ultrasonic emitting line sides, and therefore in the end face, the ultrasonic wave is reflected and at that time, a phase shift of 180° occurs. The reflected ultrasonic wave is propagated to the bonded surface side and is reflected from the bonded surface to be again propagated to the end face side while leading to the phase shift of 180°. For this reason, propagation waveforms are repeatedly generated.

A sound velocity in titanium may be changed due to shape factors such as a diameter, but a longitudinal wave is basically represented by (modulus of elasticity/density)$^{1/2}$, and therefore by substituting this value in the titanium, (modulus of elasticity/density)$^{1/2}$=$(116/4.056)^{1/2}$ [m/s]=5348 m/s.

Since the reflection wave is a plane wave going straight up to a Fresnel zone limit, in the case of obtaining a value L of the Fresnel zone limit, L=(radius)$^2$/4λ when a wavelength is defined as λ, and therefore when a radius of the titanium retarder is 10 mm at a frequency of 4 MHz, L=$(10^{-2})^2$/(4×5348/(4×$10^6$))=19 mm, and when the radius of the titanium retarder is likewise 10 mm at a frequency of 2 MHz, L=10 mm. The length of the retarder is longer than the Fresnel zone limit. In order to increase the length of the retarder, there is a need to use a material having a low sound velocity. Meanwhile, the titanium material has a lower sound velocity than other materials and therefore is advantageous. Further, in Equation representing the Fresnel zone limit, the larger the radius, the longer the length of the retarder. However, the angle (angle at which a sound pressure is 50%) of beam spread is increased according to increase of the radius of the retarder, and thus the precision of the measured flow rate is reduced. Thereby, in the viewpoint of the accurate flow rate measurement, there is a limitation in increasing the length of the retarder.

Figure 7:
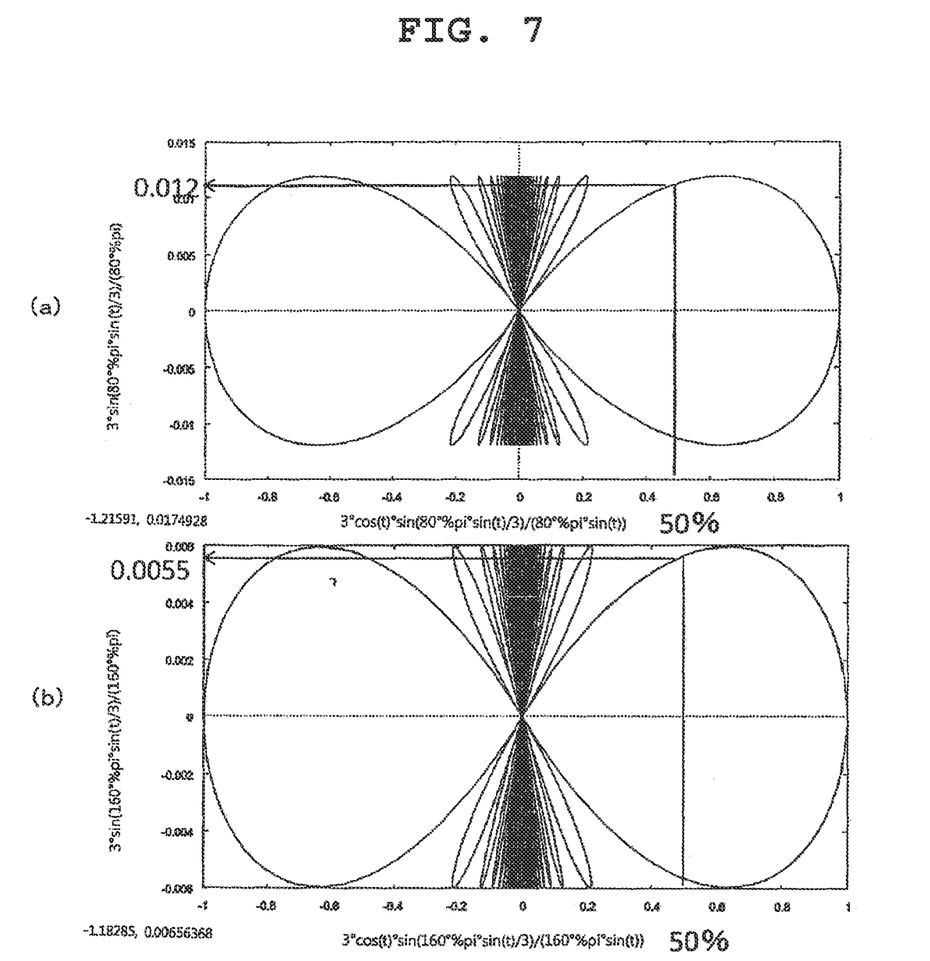

For the calculation of the angle of beam spread, an intensity of central sound field may be represented by an approximate equation of a squared, rectangular sound field having a=2 cm (corresponding to a radius of 10 mm), not a circular sound field requiring a Bessel function of the first kind. The approximate equation is represented as follows.

$$r = \frac{\sin(ka \cdot \sin\theta)}{ka \cdot \sin\theta} \quad \text{Mathematical Equation 1}$$

$$k = \frac{2\pi}{\lambda}$$

FIG. 7 illustrates a result of an approximate calculation in the rectangular sound field, in which (a) illustrates a frequency of 2 MHz, and (b) illustrates a frequency of 4 MHz. From the result, it may be appreciated that the angle of beam spread at 4 MHz is 0.63° and the angle of beam spread at 2 MHz is 1.37°.

The reflection at the boundary may be calculated from an (intrinsic) acoustic impedance of materials disposed at both sides of the boundary by a calculation equation of the Fresnel reflection. Table 3 shows the density, sound velocity, acoustic impedance of each material.

TABLE 3

|  | LiNbO$_3$ (Y36° cut plate) | Titanium | Iron | Cast Iron | Silver | Water |
| --- | --- | --- | --- | --- | --- | --- |
| Sound velocity c (m/s) | 7340 | 5348 | 5500 | 4910 | 3650 | 1480 |
| Density ρ (×10$^3$ kg/m$^3$) | 4.46 | 4.51 | 7.86 | 7.86 | 10.5 | 1 |
| Acoustic Impedance (kg/m$^2$ s) | 32.7 | 18.67 | 43 | 38.5 | 38.32 | 1.48 |

The reflection at the boundary from the titanium retarder to the silver couplant is calculated by the following Mathematical Equation 2.

$$R = \left(\frac{\rho_2 c_2 - \rho_1 c_1}{\rho_2 c_2 + \rho_1 c_1}\right)^2 = \left(\frac{38.32 - 18.67}{38.32 + 18.67}\right)^2 = 0.33^2 = 0.11 \quad \text{Mathematical Equation 2}$$

Similarly, the reflection at the boundary between the bonding layer made of silver and the LN single crystal is calculated by the following Mathematical Equation 3.

$$R = \left(\frac{\rho_2 c_2 - \rho_1 c_1}{\rho_2 c_2 + \rho_1 c_1}\right)^2 = \left(\frac{38.32 - 32.7}{38.32 + 32.7}\right)^2 = 0.08^2 = 0.006 \quad \text{Mathematical Equation 3}$$

Meanwhile, the reflection at the boundary from the silver couplant to the cast iron is represented by the following Mathematical Equation 4 and since the acoustic impedances thereof approximate each other, $$R = \left(\frac{38.59 - 38.32}{38.59 + 38.32}\right)^2 = 0.003^2 = 0.00009 \quad \text{Mathematical Equation 4}$$

the reflection is a small value which may be disregarded.

The reflection when the ultrasonic wave is output from the spool piece of cast iron to water is represented by the following Mathematical Equation 5, and $$R = \left(\frac{38.59 - 1.45}{38.59 + 1.45}\right)^2 = 0.85 \quad \text{Mathematical Equation 5}$$

15% of a non-reflection side to a total reflection wave is output to water.

Figure 8:
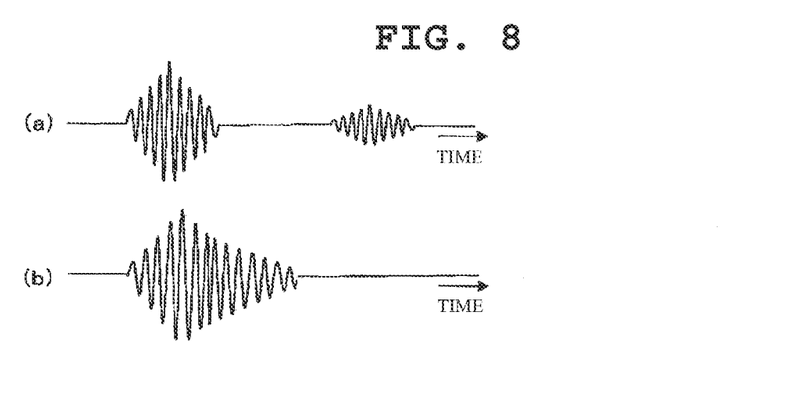

If a wave which is reflected from the boundary between the titanium retarder 3 and the couplant 4 made of silver, and is again reflected from the boundary with the piezoelectric vibrator is referred to the reflection wave, it is necessary for the titanium retarder 3 to have a length which does not occur a multiple reflection in which the reflection wave overlaps the measurement wave. FIG. 8(a) illustrates an example in which there is a sufficient time interval, and FIG. 8(b) illustrates an example in which there is no influence of the multiple reflections, but the reflection overlaps the waveform as reverberation due to the influence of the multiple reflections. For example, when the length of the titanium retarder 3 is set to be 10 mm, the frequency of the burst signal is set to be 4 MHz (time per one wave is 0.25 μs), the number of waves in the signal is set to be 5 waves, and the piezoelectric vibrator is driven at the 5 waves, and then is dumped to sink vibration at the 5 waves, as the length of the titanium retarder 3, a time corresponding to 10 waves which are two times as large as a driving waveform is at least required. This becomes 0.25×10=2.5 μs. When the length of the titanium retarder 3 is set to be 10 mm, a reciprocating propagation time of the ultrasonic wave at the retarder is 2×10×10$^{-3}$/5348=3.7 μs, and an interval with the multiple reflection wave is 12 μs. Meanwhile, when the frequency is 2 MHz, at least required time of the 10 waves is about 0.5×10=5 μs, and the multiple reflection wave overlaps the signal for measurement. When the length of the retarder is L, the frequency is f, the number of waves in the burst wave is N, and the sound velocity in the retarder is v, to prevent the influence of the multiple reflection wave, the driving time and the dumping time of the piezoelectric vibrator are the same, The relationship of (L/v)>(N/f) needs to be satisfied.

As described above, the ultrasonic sensor according to the present embodiment using the LN piezoelectric vibrator by using the silver and frit glass materials for bonding with the titanium material forming the retarder may use the Y-axis 36° cut surface which may implement the high output as the output surface of the piezoelectric vibrator, while preventing the piezoelectric vibrator from being damaged or the bonded portion from being delaminated. Further, the ultrasonic sensor uses the silver and frit glass materials used for bonding the titanium retarder as the couplant material to the piezoelectric vibrator, and as a result, there is no need to additionally dispose the couplant material later when the ultrasonic sensor is attached to the pipe or the spool piece. Further, in the titanium retarder, the dimension conditions which are not affected by the multiple reflection makes certain, and thus the high-quality signal may be processed.

DESCRIPTION OF REFERENCE NUMERALS

1: piezoelectric vibrator, 2: bonding layer
3: titanium retarder, 4: couplant
20: ultrasonic sensor, 21: pipe
22: spool piece part, 23: spool piece

The invention claimed is:

1. An ultrasonic sensor, comprising:
   a piezoelectric vibrator which is made of lithium niobate and has a surface obtained by rotating a surface orthogonal to a Y-axis of a lithium niobate crystal about an X-axis by 36°±2° as an output surface;
   a retarder made of titanium; and
   a bonding layer for bonding one surface of the retarder to the output surface,
   wherein the bonding layer is made of silver and frit glass, and
   the frit glass has a coefficient of linear expansion ranging from $5 \times 10^{-6}$ K$^{-1}$ to $15 \times 10^{-6}$ K$^{-1}$.

2. The ultrasonic sensor of claim 1, wherein the opposite surface of the retarder has a couplant layer containing silver.

3. The ultrasonic sensor of claim 2, wherein the couplant layer is made of silver and frit glass, and
   the frit glass has a coefficient of linear expansion ranging from $5 \times 10^{-6}$ K$^{-1}$ to $15 \times 10^{-6}$ K$^{-1}$.

4. The ultrasonic sensor of claim 1, wherein a mass ratio of the silver to the frit glass in the bonding layer is in a range of 79:2.3 to 82:2.5.

5. The ultrasonic sensor of claim 1, wherein the retarder is made of pure titanium inevitably including impurities.

6. The ultrasonic sensor of claim 1, wherein when a length of the retarder is L, a sound velocity in the retarder is v, a use frequency of the ultrasonic sensor is f, and the number of waves in a burst wave driving the ultrasonic sensor is N, the relationship of (L/v)>(N/f) is satisfied.

7. A manufacturing method of an ultrasonic sensor having lithium niobate as a piezoelectric vibrator, comprising:
   forming the piezoelectric vibrator which has a surface obtained by rotating a surface orthogonal to a Y-axis of a lithium niobate crystal about an X-axis by 36°±220 as an output surface, and is prepared by applying a silver paste to at least the output surface and burning the same;
   applying the silver paste to one surface and the other surface of a titanium retarder which are opposite to each other; and
   contacting one surface of the retarder with the output surface of the burned piezoelectric vibrator, and then performing burning the same under an inert gas atmosphere at a predetermined temperature or more,
   wherein the silver paste applied to the output surface and the one surface of the retarder includes silver and frit glass, and the frit glass has a coefficient of linear expansion ranging from $5 \times 10^{-6}$ K$^{-1}$ to $15 \times 10^{-6}$ K$^{-1}$.

8. The method of claim 7, wherein a composition of the silver paste applied to the other surface of the retarder is the same as that of the silver paste applied to the one surface thereof.

9. The method of claim 7, wherein the silver paste includes an organic binder, and a mass ratio of the silver to the frit glass in the silver paste has a value ranging from 79:2.3 to 82:2.5.

* * * * *